United States Patent [19]

Etes

[11] 4,182,478
[45] Jan. 8, 1980

[54] DISPOSABLE EMESIS CONTAINER

[75] Inventor: Donald E. Etes, Crystal Lake, Ill.

[73] Assignee: North American Laboratories, Inc., Crystal Lake, Ill.

[21] Appl. No.: 971,938

[22] Filed: Dec. 21, 1978

[51] Int. Cl.² .............................................. B65D 33/24
[52] U.S. Cl. ...................................... 229/62; 229/62.5
[58] Field of Search ...................... 229/62, 62.5; 150/3, 150/9

[56] References Cited

U.S. PATENT DOCUMENTS

| | | | |
|---|---|---|---|
| 2,177,919 | 10/1939 | Vogt | 229/62 |
| 2,943,660 | 7/1960 | Seeger | 150/3 |
| 3,366,312 | 1/1968 | Lowenberg et al. | 229/62 |
| 3,502,258 | 3/1970 | Kugler et al. | 229/62 X |
| 3,797,734 | 3/1974 | Fleury et al. | 229/62.5 |

*Primary Examiner*—Stephen P. Garbe

*Attorney, Agent, or Firm*—Lockwood, Dewey, Alex & Cummings

[57] ABSTRACT

An improved disposable emesis container comprising a bag with its upper end enclosing the wide bottom of a funnel formed of paperboard-like material. The containers are mass-produced in a flattened collapsed condition. In use the funnel is squeezed open and after use generally elliptical complementary panels formed on the upper end of the funnel are folded over on each other to provide a self-retaining closure. The lower end of the funnel has downwardly arcuate score lines in the opposite sides which upon being pressed together following formation of the self-retaining closure, act in cooperation with the closure to close together the opposing bottom edges of the wide bottom of the funnel thereby providing a closed valve within the upper end of the bag so as to retain contents of the bag therein.

2 Claims, 5 Drawing Figures

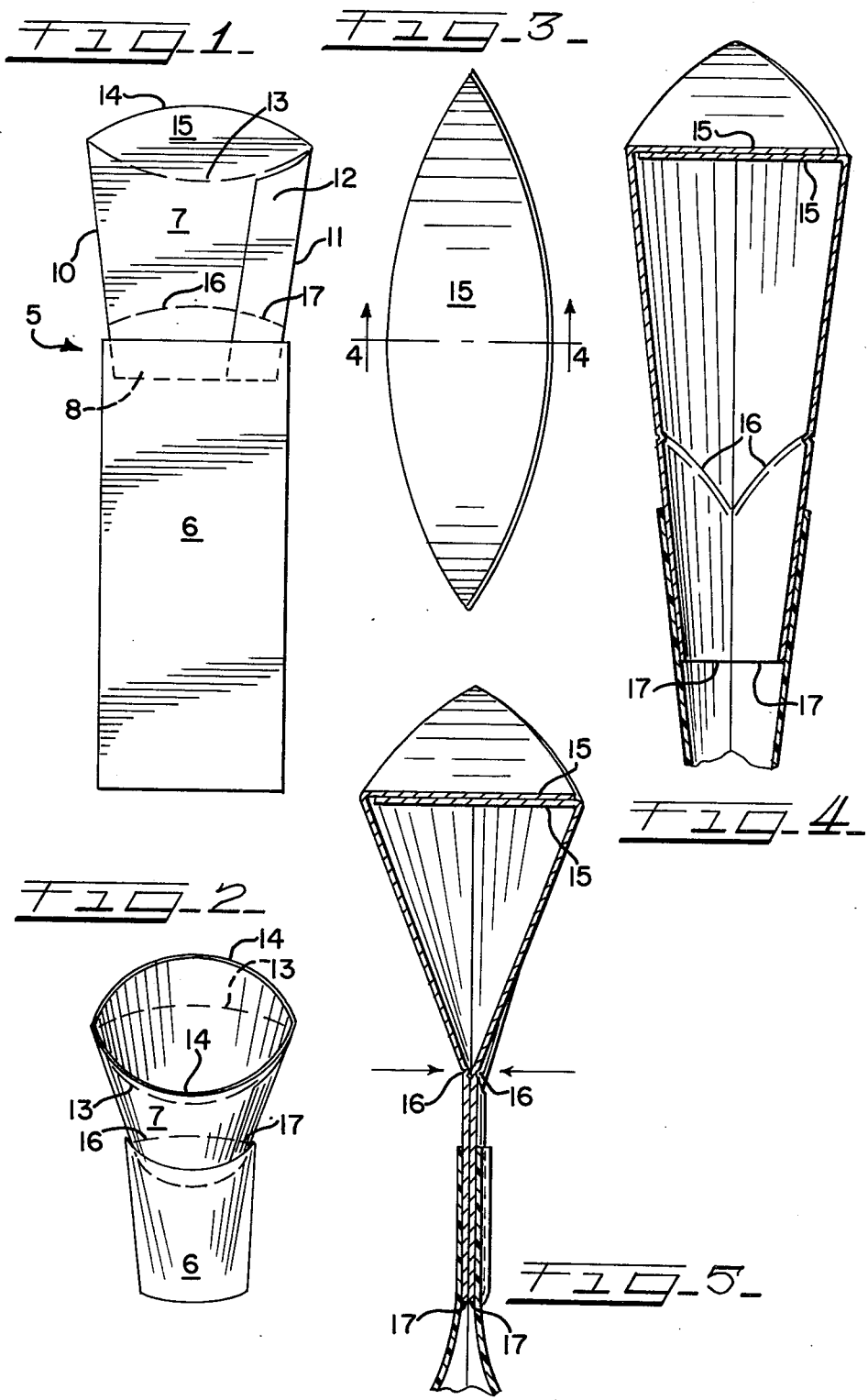

DISPOSABLE EMESIS CONTAINER

This invention relates generally to an improved disposable emesis container for general use in: emergency rooms to collect emesis from poison victims; sick rooms; boats; airplanes; automobiles; etc.

The object of the invention, generally states is the provision of improved disposable emesis containers of the class described which are economical to produce, convenient to use, exhibit good retention characteristics for contents after use and closure, and which have a simplified construction in respect to prior disposable emesis containers.

Other and more specific objects of the invention will be apparent from the following detailed description of the invention including a presently preferred embodiment thereof.

The invention relates specifically to an improved disposable emesis container of the type shown and described in U.S. Pat. No. 3,797,734 dated Mar. 19, 1974. However, the containers of the present invention have fewer essential components and are simpler and more economical to produce than those shown and described in U.S. Pat. No. 3,797,734.

For a more complete understanding of the nature and scope of the invention, reference may now be had to the following detailed description of the presently preferred embodiment thereof taken in connection with the accompanying drawings wherein:

FIG. 1 is an elevational view of a disposable emesis container made in accordance with the present invention showing the container in its as-manufactured, unused, flattened, collapsed condition.

FIG. 2 is a downward perspective view of the container of FIG. 1 in its opened, ready-to-use condition.

FIG. 3 is a top plan view of the container of FIG. 1 after it has been used and the upper end thereof has been actuated to its closed condition.

FIG. 4 is a fragmentary vertical sectional view taken on line 4—4 of FIG. 3.

FIG. 5 is a view similar to FIG. 4 but showing the container after the bottom portions of the funnel have been pressed together below arcuate score lines so as to close together the bottom edges of the funnel portion.

In the drawings, the disposable emesis container is indicated generally at 5 and comprises two components, a bag 6 and a funnel 7. The bag 6 may be formed of any suitable disposable bag-forming material including various plastic films such as polyurethane, polyethelyne or polypropylene, and coated paper. The bag 6 should, however, be formed of a material which has adequate liquid retention properties so as not to leak or break with normal handling. The funnel 7 has a wide bottom 8 and is formed of a relatively stiff sheet material of the character of paperboard or other sheet material such as plastics having paperboard-like properties in respect to flexibility and stiffness.

The mouth or upper end of the bag 6 is wide enough so as to fit over the lower end of the funnel 7 and is suitably secured thereto in a suitable liquid-tight manner. For example, if the funnel 7 is formed of paperboard having a suitable coating, the upper end of the bag 6 may be heat sealed to the lower end of the funnel 7. Otherwise, a suitable adhesive material may be used to form the permanent connection which should be liquid tight to a reasonable degree.

The funnel 7 is formed from a blank of suitable material such as coated paperboard and then is suitably folded so as to have opposing side creases 10 and 11 in the flattened condition. The blank will normally have sufficient length so that a flap 12 on one end will overly the opposite end of the blank and may be suitably secured thereto by adhesive, heat sealing or other known adhering techniques.

It will be readily apparent and understood that both the bags 6 and the funnels 7 can be mass-produced at low cost and can be readily assembled together in the flattened collapsed condition as shown in FIG. 1. In the production of the blank from which the funnel 7 is formed there will be formed upwardly arcuate or concave scorelines 13—13 in the opposed flattened sides of the funnel 7 with the ends of these score lines 13 joining or connecting with the respective convex free upper edges 4 so as to form at the top or mouth of the funnel 7 generally elliptical complementary panels 15 with pointed ends in opposite sides thereof. The panels 15 overly each other in the flattened condition of the funnel 7 and the score lines 13—13 will be juxtaposed or in registration with each other as will also the upper edges 14.

Adjacent the bottom end of the funnel 7 there are formed in the opposite sides thereof downwardly arcuate score lines 16—16. These score lines will normally be formed in the blank from which the funnel 7 is produced. It is desirable that a weakened perforated score line 17 be formed in the flap 12 where it overlaps the end of the score line 16 underneath the flap 12. This weakened line 17 permits the funnel 7 to be collapsed and opened without interfering with the normal action of the funnel material.

In the use of one of the disposable emesis containers 5, the user grasps the funnel portion 7 and presses or squeezes inwardly on the opposite edges or creases 10 and 11 thereby opening the funnel 7 and allowing emesis or other material to be discharged into the bag 7 through the funnel. The wide mouth of the funnel makes it easy for the user to direct the emesis into the container 5. It will be seen that the funnel 7 serves as a convenient handle allowing the user to make convenient use of the container 5 without any additional attachment or support.

After use of the container 5, the upper end is closed by folding the panels 15 inwardly over on one another as permitted by the score lines 13. It is not important which of the panels 15 is first folded inwardly. After they have been folded inwardly, the panels 15 will overly each other as shown in FIGS. 4 and 5. Because of the arcuate curvature of the score lines 13 the overlying panels 15 have an over-center-like or toggle-like action so that they retain their folded-over closed position and thereby provide a closure for the upper end of the container 5. However, the bottom 8 of the funnel 7 will still be open and remain open with the opposed bottom edges 19—19 separated as shown in FIG. 4 after the panels 15 have been folded-over on each other. It is desirable that the bottom end 8 be closed in order to prevent material from within the bag 7 from escaping from the container in the event it is not maintained in a suspended upright condition. The bottom end 8 can be brought to a closed condition by pressing together the funnel 7 from opposite sides adjacent the downwardly arcuate score lines 16. Upon pressing together the opposed score lines 16, the bottom portion of the funnel 7 below the score lines will assume and retain a collapsed condition with the bottom edges 17 of the funnel closed together. This closed condition is shown and illustrated in FIG. 5.

After the score lines 16 have been pressed inwardly together following the folding over of the panels 15, the container 5 will be sufficiently closed so that it can be laid on its side without danger of the contents escaping.

What is claimed is:

1. In a disposable emesis container consisting of a bag and a wide bottom funnel with the mouth of the bag fitting over and secured to the bottom of the funnel, said bag and funnel having a normally flattened collapsed empty condition, said funnel being formed of a material having paperboard-like stiffness and flexibility with the convex upper edges thereof juxtaposed in the flattened condition of the funnel, said funnel having juxtaposed concave score lines formed in the opposite sides thereof in the flattened condition with the opposite ends thereof terminating at the opposite ends of said convex upper edges, and said convex upper edges and their associated concave score lines forming generally elliptical panels with pointed ends at the mouth of said funnel which upon being inwardly folded-over one another provide a self-retaining closure for said container, the improvement which comprises: downwardly arcuate score lines in the opposite sides of said funnel adjacent said wide bottom thereof which are juxtaposed in registration in the flattened collapsed condition of the funnel and which upon being pressed together when said funnel is open but after said generally elliptical panels have been folded-over on each other, act to close together the bottom edges of said wide bottom.

2. In the improved disposable emesis container called for in claim 1 said funnel having an overlap and said overlap having a weakened score line therein overlying a portion of one of said downwardly arcuate score lines.

* * * * *